(12) United States Patent
Jiang et al.

(10) Patent No.: US 10,676,709 B2
(45) Date of Patent: Jun. 9, 2020

(54) FLOWABLE MICROBIAL OIL

(71) Applicant: Mara Renewables Corporation, Dartmouth (CA)

(72) Inventors: Xuan Jiang, Dartmouth (CA); Dorothy Dennis, Dartmouth (CA); Roberto E. Armenta, Dartmouth (CA)

(73) Assignee: MARA Renewables Corporation, Dartmouth (CA)

( * ) Notice: Subject to any disclaimer, the term of this patent is extended or adjusted under 35 U.S.C. 154(b) by 427 days.

(21) Appl. No.: 15/655,287

(22) Filed: Jul. 20, 2017

(65) Prior Publication Data

US 2018/0023047 A1   Jan. 25, 2018

Related U.S. Application Data

(60) Provisional application No. 62/364,455, filed on Jul. 20, 2016.

(51) Int. Cl.
| | |
|---|---|
| *C12N 1/26* | (2006.01) |
| *C11B 1/02* | (2006.01) |
| *C12N 1/12* | (2006.01) |
| *C07C 7/10* | (2006.01) |
| *C11B 1/10* | (2006.01) |

(52) U.S. Cl.
CPC .............. *C12N 1/26* (2013.01); *C07C 7/10* (2013.01); *C11B 1/02* (2013.01); *C11B 1/10* (2013.01); *C12N 1/12* (2013.01)

(58) Field of Classification Search
None
See application file for complete search history.

(56) References Cited

U.S. PATENT DOCUMENTS

| | | | |
|---|---|---|---|
| 4,889,740 A * | 12/1989 | Price | A23D 9/00 426/606 |
| 5,340,594 A | 8/1994 | Barclay | |
| 5,340,742 A | 8/1994 | Barclay | |
| 6,607,900 B2 | 8/2003 | Bailey et al. | |
| 8,163,515 B2 | 4/2012 | Burja et al. | |
| 9,745,538 B2 * | 8/2017 | Dennis | C12P 7/6427 |
| 2009/0117194 A1 | 5/2009 | Burja et al. | |
| 2012/0244584 A1 | 9/2012 | Zhang et al. | |
| 2015/0176042 A1 | 6/2015 | Dennis et al. | |
| 2016/0102328 A1 | 4/2016 | Park et al. | |

FOREIGN PATENT DOCUMENTS

WO    9408467    4/1994

OTHER PUBLICATIONS

PCT/IB2017/054411, "International Search Report and Written Opinion", dated Nov. 1, 2017, 8 pages.
Puri P.S. 1980. Winterization of oils and fats. Journal of the American Oil Chemists Society (1980) 57(11):A848-A850.
EP17830588.4, "Extended European Search Report", dated Jan. 21, 2020, 9 pages.
Raghukumar, "Thraustochytrid Marine Protists: Production of Pufas and Other Emerging Technologies", Marine Biotechnology, vol. 10, No. 6, 2008, pp. 631-640.
CA3,031,177, "Office Action", dated Jan. 7, 2020, 3 pages.
IN201917004543, "First Examination Report", dated Dec. 23, 2019, 4 pages.

* cited by examiner

*Primary Examiner* — Heidi Reese

(74) *Attorney, Agent, or Firm* — Kilpatrick Townsend & Stockton LLP

(57) ABSTRACT

Provided herein is a method for obtaining flowable oil comprising the steps of providing a population of oil-producing microorganisms; recovering oil from the microorganisms, wherein the oil is at a first temperature; reducing the first temperature over a first period of time to a second temperature; and applying mechanical energy to the oil during the first period of time thereby producing the flowable oil.

22 Claims, 1 Drawing Sheet

FLOWABLE MICROBIAL OIL

CROSS-REFERENCE TO RELATED APPLICATION

This application claims priority to U.S. Provisional Application No. 62/364,455, filed Jul. 20, 2016, which is incorporated by reference herein in its entirety.

BACKGROUND

Microbial oils have attracted more and more attention as a sustainable source of nutritional oils, i.e., omega-3 fatty acids. The increasing awareness of the health benefits of these nutritional oils has led to great demand for the oil in dietary supplements, nutraceuticals, and food. Refining processes have been developed and established in specialized refineries to meet market demands and requirements. However, crude microbial oil solidifies upon cooling to ambient conditions making it difficult to handle. Typically, additives are added or additional process steps are performed to remove components from the oil are included to improve the flowability of the oil.

BRIEF SUMMARY

Provided herein is a method for obtaining flowable oil comprising the steps of providing a population of oil-producing microorganisms; recovering oil from the microorganisms, wherein the oil is at a first temperature; reducing the first temperature of the oil over a first period of time to a second temperature and applying mechanical energy to the oil during the first period of time thereby producing the flowable oil.

BRIEF DESCRIPTION OF THE DRAWINGS

(FIG. 1A) flowable oil, (FIG. 1B) solid oil cooled at 20° C.

DETAILED DESCRIPTION

After oils are produced and extracted, cool conditions lead to instant oil supersaturation and a high rate of nucleation of the oil, resulting in high viscosity and eventually oil solidification. Even when the oil is cooled slowly, it tends to form an extremely thick paste. This is mainly attributed to evenly distributed crystals formed during the cooling process and the strong network they form. Until the present method, this viscosity and solidification was avoided with additives or extra processing steps. It is not always desirable to modify the flowability of the oil by adding additives that may affect food safety and require subsequent removal, and additional processing steps can lead to significant oil loss. Provided herein is a process that changes the flowability of an oil that tends to solidify at room temperature without removing any components from the oil or adding any ingredients to it. For example, components that can be removed include longer chain saturated fatty acids that are solid at room and that can be removed by fractionation. Exemplary ingredients that can be added to oil to increase its flowability include, but are not limited to, oil thinners, organic solvents and lighter oils (e.g. high-oleic oil, C18:1). The herein provided methods change the flowability of the oil while maintaining the constituents thereof.

Figure 1A:
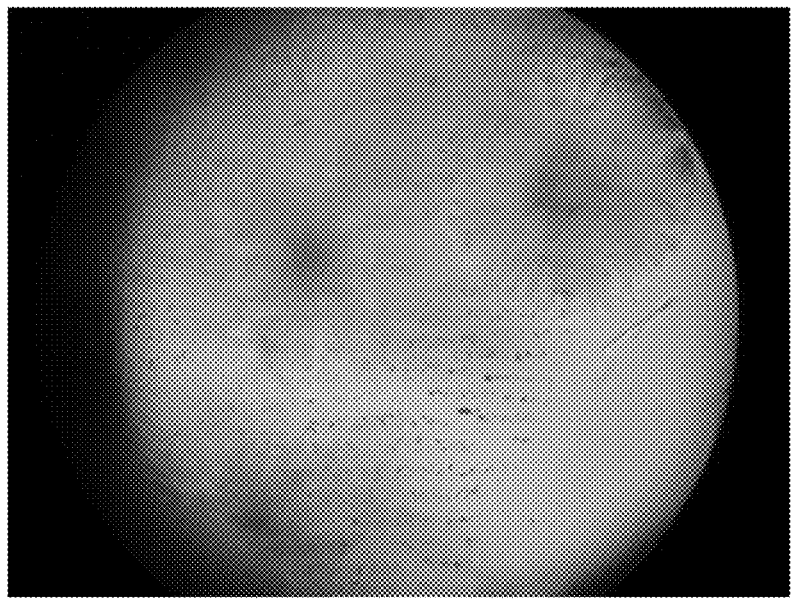
FIG. 1A and 1B are images of oil crystals under microscope (×400 times magnification).
Figure 1B:
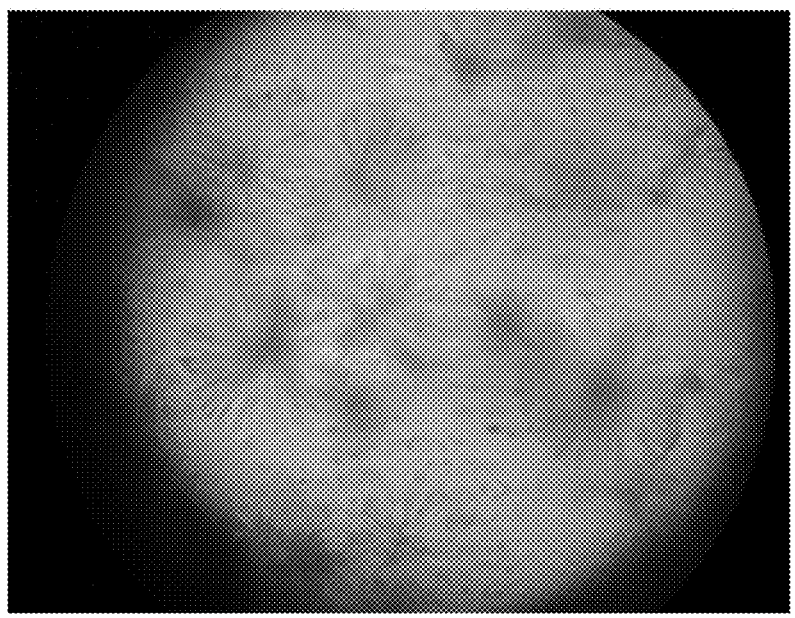

Without meaning to be limited by theory, the process is a cooling treatment with a simultaneous input of selective mechanical energy to achieve a quick oil crystal growth and microstructure form modification. The mechanical energy encourages crystal transition to more stable crystal forms, which lowers oil viscosity. Moreover, the mechanical energy pulls solids in one way and releases liquid oil from the crystals' network, which permits the movement of liquid oil fractions. Once the solid and liquid phase are established, gentle mixing allows the two phases to co-exist in flowable form. Stated another way, the provided flowability process changes the oil microstructure by applying a selective mechanical energy that promotes the formation of stable crystal forms and the weakening of the crystal networks. The crystals in the flowable oil are much larger than those formed in oil cooled naturally (FIG. 1). The larger, but reduced amount of crystals, weakens particle interactions, thus enabling liquid oil movement. The solids find support and float inside of the liquid oil droplets. Obtained flowable oils through the disclosed method remained liquid at room temperature as well as after storing them at 4° C. The provided flowable oil is easier to use as it can be poured or pumped making oil transfer to refineries easier. By using the herein described oil flowability manipulation method, no changes take place with regard to the oil composition and, optionally, no additives are added that could be difficult to remove later.

Provided herein is a method for obtaining flowable oil comprising the steps of providing a population of oil-producing microorganisms; recovering oil from the microorganisms, wherein the oil is at a first temperature; reducing the first temperature of the oil over a first period of time to a second temperature; and applying mechanical energy to the oil during the first period of time thereby producing the flowable oil, wherein the method is carried out without further purification steps and in the absence of agents that decrease oil viscosity. Optionally, the composition of the oil remains unchanged prior to reducing the first temperature of the oil. Optionally, the method further comprises storing the oil at a third temperature for a third period of time. Optionally, the third temperature is room temperature (i.e., about 18 to 23° C., e.g., about 20° C.). Optionally, the third temperature is about 4° C. Optionally, the oil comprises one or more polyunsaturated fatty acids. Optionally, the polyunsaturated fatty acid is docosahexaenoic acid (DHA).

Oil flowability or cold flow oil properties can be characterized by three different points or temperatures: the melting point, the cloud point and the pour point. As used herein, the term melting point refers to the temperature at which the oil becomes clear. As used herein, the term cloud point refers to the temperature of the oil at which the oil begins to crystalize. As used herein, the pour point is an index of the lowest temperature at which movement of the test specimen (e.g., oil) is observed under prescribed conditions of test. These temperatures can be determined by known methods including those established by the American Oil Chemistry Society (AOCS) and American Society of Testing and Materials (ASTM), which establishes specifications for determining the melting, cloud and pour points of fluids such as lipids and oils. For example, melting point can be determined using AOCS Official Method Cc 1-25, cloud point can be determined using AOCS Official Method Cc 6-25, and pour point can be determined using ASTM Official Method D97. Typically, the pour point of oil is above room temperature. The provided methods result in an oil that is flowable at or below about room temperature. Optionally, the oil is flowable at about 4° C.

In the provided methods, the first temperature is typically above the melting point of the oil. Optionally, the first temperature is from 30° C. to 60° C. Thus, the first temperature can be any degree between and including 30° C. and 60° C. Thus, the first temperature can be 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60° C. or any fraction thereof, e.g., 49.1, 49.2, 49.3, 49.4, 49.5, 49.6, 49.7, 49.8, 49.9 or 50.0.

The oil can be maintained at the first temperature for a period of time. Optionally, the oil is maintained at the first temperature for 1 to 60 or more minutes. Thus, the oil can be maintained at the first temperature for any time between 1 and 60 minutes or for more than 60 minutes. Optionally, the oil is maintained at the first temperature for any time between 5 and 60 minutes.

In the provided methods, the oil is reduced from the first temperature to the second temperature over a first period of time. Optionally, the first period of time is from 1 to 30 minutes. The first period of time can be any value between 1 and 30 minutes. Optionally, the first period of time is 5 to 30 minutes. Thus, the first period of time can be 1, 5, 10, 15, 20, 25, or 30 minutes or any fractional value therein. Optionally, the first temperature is reduced by 0.5 to 5 degrees per minute over the first period of time to the second temperature.

Optionally, the second temperature of the oil is −10° C. to 30° C. inclusive. Optionally, the second temperature of the oil is 0 to 9° C. or any temperature between 0 to 9° C. Optionally, the second temperature of the oil is 5° C.

The oil can be maintained at the second temperature for 1 to 30 minutes. Optionally, the oil is maintained at the second temperature for 5 to 30 minutes. Thus, the oil can be maintained at the second temperature can be 1, 5, 10, 15, 20, 25, or 30 minutes or any fractional value therein.

Optionally, the oil is stored at a third temperature for a third period of time. Optionally, the third temperature is about room temperature. Optionally, the third temperature is 0 to 5° C., e.g., about 4° C.

The mechanical energy can be applied by any suitable means to reach the desired outcome. Optionally, the mechanical energy is applied by centrifugation, stirring, mixing, blending, shaking, vibrating, or any combination thereof. Optionally, the mechanical energy comprises mixing at a speed of 50 to 200 rpm. Optionally, the mechanical energy comprises centrifugation.

The mechanical energy produces a population of crystals with an average particle size larger than crystals produced in the absence of the mechanical energy. Optionally, the population of crystals of the flowable oil are 15-60 µm in diameter.

Optionally, the provided methods comprise providing the oil at a temperature above the melting point of the oil and reducing the temperature of the oil over a period of time while applying mechanical energy to the oil to a temperature below the melting point of the oil and storing the oil at a third temperature. Optionally, the mechanical energy is centrifugation. Optionally, the third temperature is about room temperature. Optionally, the third temperature is 0 to 5° C., e.g., about 4° C.

Oil that is processed using the provided methods can be obtained from a variety of sources including, for example, microorganisms. Optionally, the oil is a plant seed oil. Suitable microorganisms that can be used to produce oil that is processed in the provided methods include, but are not limited to, oil producing algae (e.g., microalgae), fungi (including yeast), bacteria, or protists. Optionally, the population of microorganisms is selected from the genus *Oblongichytrium, Aurantiochytrium Thraustochytrium,* and *Schizochytrium* or any combination thereof. Optionally, the microorganism includes Thraustochytrids of the order Thraustochytriales, more specifically Thraustochytriales of the genus *Thraustochytrium*. Optionally, the population of microorganisms includes Thraustochytriales as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18) as described in U.S. Pat. No. 8,163,515, which is incorporated by reference herein in its entirety.

Microalgae are acknowledged in the field to represent a diverse group of organisms. For the purpose of this document, the term microalgae is used to describe unicellular microorganisms derived from aquatic and/or terrestrial environments (some cyanobacteria are terrestrial/soil dwelling). Aquatic environments extend from oceanic environments to freshwater lakes and rivers, and also include brackish environments such as estuaries and river mouths. Microalgae can be photosynthetic; optionally, microalgae are heterotrophic. Microalgae can be of a eukaryotic nature or of a prokaryotic nature. Microalgae can be non-motile or motile.

The term thraustochytrid, as used herein, refers to any member of the order Thraustochytriales, which includes the family Thraustochytriaceae. Strains described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporuni*), *Japonochytrium* (Species: sp., *marinum*), *Aplanochytrium* (Species: sp., *haliotidis, kerguelensis, profunda, stocchinoi*), *Althornia* (Species: sp., *crouchii*), or *Elina* (Species: sp., *marisalba, sinorifica*). Species described within *Ulkenia* will be considered to be members of the genus *Thraustochytrium*. Strains described as being within the genus *Thrautochytrium* may share traits in common with and also be described as falling within the genus *Schizochytrium*. For example, in some taxonomic classifications ONC-T18 may be considered within the genus *Thrautochytrium,* while in other classifications it may be described as within the genus *Schizochytrium* because it comprises traits indicative of both genera.

The provided methods include or can be used in conjunction with additional steps for culturing microorganisms according to methods known in the art and obtaining the oil therefrom. For example, a Thraustochytrid, e.g., a *Thraustochytrium* sp., can be cultivated according to methods described in U.S. Patent Publications 2009/0117194 or 2012/0244584, which are herein incorporated by reference in their entireties for each step of the methods or composition used therein. The oil obtained from the microorganisms can then be further processed in accordance with the methods described herein. Optionally, the oil comprises triglycerides. Optionally, the oil comprises alpha linolenic acid, arachidonic acid, docosahexanenoic acid, docosapentaenoic acid, eicosapentaenoic acid, gamma-linolenic acid, linoleic acid, linolenic acid, or a combination thereof.

Microorganisms are grown in a growth medium (also known as culture medium). Any of a variety of media can be suitable for use in culturing the microorganisms described herein. Optionally, the medium supplies various nutritional components, including a carbon source and a nitrogen source, for the microorganism. Medium for Thraustochytrid culture can include any of a variety of carbon sources. Examples of carbon sources include fatty acids, lipids, glycerols, triglycerols, carbohydrates, polyols, amino sugars, and any kind of biomass or waste stream.

Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine.

Optionally, the microorganisms provided herein are cultivated under conditions that increase biomass and/or production of a compound of interest (e.g., oil or total fatty acid (TFA) content). Thraustochytrids, for example, are typically cultured in saline medium. Optionally, Thraustochytrids can be cultured in medium having a salt concentration from about 0.5 g/L to about 50.0 g/L. Optionally, Thraustochytrids are cultured in medium having a salt concentration from about 0.5 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 0.5 g/L to about 20 g/L (e.g., from about 0.5 g/L to about 15 g/L). The culture medium optionally includes NaCl. Optionally, the medium includes natural or artificial sea salt and/or artificial seawater.

The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is supplied by sodium chloride.

The medium, for example, for Thraustochytrids culture, can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Optionally, the resulting biomass is pasteurized to inactivate undesirable substances present in the biomass. For example, the biomass can be pasteurized to inactivate compound degrading substances. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 140° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means, such as, for example, by direct steam injection.

Optionally, no pasteurization step is performed. Stated differently, the method disclosed herein optionally lacks a pasteurization step.

Optionally, the biomass can be harvested according to a variety of methods, including those currently known to one skilled in the art. For example, the biomass can be collected from the fermentation medium using, for example, centrifugation (e.g., with a solid-ejecting centrifuge) or filtration (e.g., cross-flow filtration). Optionally, the harvesting step includes use of a precipitation agent for the accelerated collection of cellular biomass (e.g., sodium phosphate or calcium chloride).

Optionally, the biomass is washed with water. Optionally, the biomass can be concentrated up to about 30% solids. For example, the biomass can be concentrated to about 5% to about 20% solids, from about 7.5% to about 15% solids, or from about solids to about 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

The oil or polyunsaturated fatty acids are obtained or extracted from the biomass or microorganisms using one or more of a variety of methods, including those currently known to one of skill in the art. For example, methods of isolating oil or polyunsaturated fatty acids are described in U.S. Pat. No. 8,163,515, which is incorporated by reference herein in its entirety. Alternatively, the oil or polyunsaturated fatty acids are isolated as described in U.S. Publication No.

2015-0176042, which is incorporated by reference herein in its entirety. Optionally, the one or more polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

Oil including polyunsaturated fatty acids (PUFAs) and other lipids produced according to the method described herein can be utilized in any of a variety of applications exploiting their biological, nutritional, or chemical properties. Optionally, the oil is used to produce fuel, e.g., biofuel. Optionally, the oil is used in pharmaceuticals, food supplements, animal feed additives, cosmetics, and the like. Lipids produced according to the methods described herein can also be used as intermediates in the production of other compounds.

By way of example, the oil produced by the microorganisms cultured using the provided methods can comprise fatty acids (e.g., PUFAs). Optionally, the fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and any combinations thereof. Optionally, the oil comprises triglycerides. Optionally, the oil comprises fatty acids selected from the group consisting of palmitic acid (C16:0), myristic acid (C14:0), palmitoleic acid (C16:1(n-7)), cis-vaccenic acid (C18:1(n-7)), docosapentaenoic acid (C22:5(n-6)), docosahexaenoic acid (C22:6(n-3)), and any combination thereof.

Optionally, the lipids produced according to the methods described herein can be incorporated into a final product (e.g., a food or feed supplement, an infant formula, a pharmaceutical, a fuel, etc.). Suitable food or feed supplements into which the lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, a lipid produced according to the method described herein can be included in a dietary supplement and optionally can be directly incorporated into a component of food or feed (e.g., a food supplement).

Examples of foodstuffs into which lipids produced by the methods described herein can be incorporated include animal feed (pet foods such as cat foods, dog foods, feeds for aquarium fish, cultured fish or crustaceans, and the like); feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFAs) can be incorporated into a nutraceutical or pharmaceutical product or a cosmetic. Examples of such a nutraceuticals or pharmaceuticals include various types of tablets, capsules, drinkable agents, etc. Optionally, the nutraceutical or pharmaceutical is suitable for topical application (e.g., in a lotion or ointment). Dosage forms can include, for example, capsules, oils, granula, granula subtilae, pulveres, tabellae, pilulae, trochisci, or the like.

The oil or lipids produced according to the methods described herein can be incorporated into products as described herein in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

All ranges as recited herein include each and every value or fractional value within the range and are inclusive of their end points.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLE

Example 1. Manipulation of Flowability of Oil Using Centrifugation

Testing was conducted at bench scale to replicate pilot plant production conditions. Cooling and oil crystal aggregation were intentionally conducted by temperature control and simultaneous centrifugation. It was found that centrifugation at a temperature at 10° C. and above did not render the oil flowable in the following day's observation. However, centrifugation at temperature as low as 5° C. produced flowable oil. Additional tests were carried out to confirm the repeatability of the results as well as to rule out other debatable conditions, e.g., stationary cooling. The flowable oils obtained were placed at 4° C. to challenge its cold flow property and flowability was maintained. The crystals in the flowable oil were much larger than those formed in oil cooled naturally (FIG. 1). The larger, but reduced amount of crystals, presumably weakened particle interactions enabling liquid oil movement. Thus, the solids find support and float inside the liquid oil. Obtained flowable oils remained liquid (i.e., flowable) at room temperature as well as after storing them at 4° C. for a week.

Example 2. Manipulation of Flowability of Oil by Mixing

To determine whether other types of mechanical energy are effective, oil was heated to 50° C. and maintained for 10 minutes. The oil was cooled to 5° C. or 15° C. and stirred at 350 rpm or 60 rpm for 20 minutes. The oil was placed a room temperature and flowability was determined the following day. Oil treated to 60 rpm and 5° C. was flowable. Increasing the rpm at 5° C. to 350 resulted in semi-solid oil. Oil mixed at 60 or 350 rpm at 15° C. was not flowable.

What is claimed is:

1. A method for obtaining flowable oil comprising the steps of providing a population of oil-producing microorganisms; recovering oil from the microorganisms, wherein the oil is at a first temperature; reducing the first temperature over a first period of time to a second temperature; and applying mechanical energy to the oil during the first period of time thereby producing the flowable oil, wherein the method is carried out without further purification steps and in the absence of agents that decrease oil viscosity.

2. The method of claim 1, wherein the oil is maintained at the first temperature for 5 to 60 minutes.

3. The method of claim 1, wherein the first temperature is above the melting point of the oil.

4. The method of claim 1, wherein the first temperature is from 30° C. to 60° C.

5. The method of claim 1, wherein the first period of time is 5 to 30 minutes.

6. The method of claim 1, wherein the second temperature is −10° C. to 30° C.

7. The method of claim 1, wherein the second temperature is 0 to 9° C.

8. The method of claim 1, wherein the second temperature is 5° C.

9. The method of claim 1, wherein the first temperature is reduced by 0.5 to 5 degrees per minute over the first period of time to the second temperature.

10. The method of claim 1, wherein the oil is maintained at the second temperature for 5 to 30 minutes.

11. The method of claim 1, wherein the mechanical energy is applied by mixing, shaking or centrifugation.

12. The method of claim 11, wherein the mixing comprises a speed of 50 to 200 rpm.

13. The method of claim 1, wherein the mechanical energy produces a population of crystals with an average particle size larger than crystals produced in the absence of the mechanical energy.

14. The method of claim 13, wherein the population of crystals of the flowable oil are 15-60 μm in diameter.

15. The method of claim 1, wherein the oil comprises one or more polyunsaturated fatty acids.

16. The method of claim 15, wherein the polyunsaturated fatty acid is docosahexaenoic acid (DHA).

17. The method of claim 1, wherein the oil is derived from a population of microorganisms selected from the group consisting of algae, fungi, bacteria and protists.

18. The method of claim 17, wherein the population of microorganisms is selected from the genus *Oblongichytrium, Aurantiochytrium Thraustochytrium,* and *Schizochytrium* or any combination thereof.

19. The method of claim 18, wherein the population of microorganisms is *Thraustochytrium* sp. deposited as ATCC Accession No. PTA-6245.

20. The method of claim 1, wherein the method further comprises storing the oil at a third temperature for a third period of time.

21. The method of claim 20, wherein the third temperature is room temperature.

22. The method of claim 20, wherein the third temperature is 4° C.

* * * * *